United States Patent

Hawlina

[11] Patent Number: 5,154,174
[45] Date of Patent: Oct. 13, 1992

[54] ELECTRODE FOR ELECTRORETINOGRAPHY AND METHOD OF USE

[76] Inventor: Marko Hawlina, OB Zeleni Jami 3, 61000 Ljubljana, Yugoslavia

[21] Appl. No.: 686,235

[22] Filed: Apr. 16, 1991

[30] Foreign Application Priority Data

Apr. 20, 1990 [GB] United Kingdom ............... 9008901

[51] Int. Cl.⁵ .............................................. A61B 5/04
[52] U.S. Cl. .................................. 128/639; 128/642
[58] Field of Search .............. 128/639, 642, 640, 712, 128/731, 744, 745, 793, 739, 644, 802, 784-786

[56] References Cited

U.S. PATENT DOCUMENTS

| | | | |
|---|---|---|---|
| 3,568,662 | 3/1971 | Euerett et al. | 128/639 |
| 4,131,113 | 12/1978 | Fender et al. | 128/745 |
| 4,386,831 | 6/1983 | Grounauer | 128/745 |
| 4,417,581 | 11/1983 | Dawson | 128/639 |
| 4,633,889 | 1/1987 | Talalla et al. | 128/784 |
| 4,735,207 | 4/1988 | Nambu et al. | 128/639 |
| 4,800,898 | 1/1989 | Hess et al. | 128/785 |
| 4,874,237 | 10/1989 | Cringle | 128/639 |
| 4,959,130 | 9/1990 | Josowicz et al. | 128/639 |

FOREIGN PATENT DOCUMENTS

| | | | |
|---|---|---|---|
| 0096330 | 12/1983 | European Pat. Off. | 128/639 |
| 0194598 | 9/1986 | European Pat. Off. | 128/639 |

*Primary Examiner*—Kyle L. Howell
*Assistant Examiner*—J. R. Jastrzab
*Attorney, Agent, or Firm*—Michael J. DeSha

[57] ABSTRACT

An electrode for electroretinography comprises a plastically deformable, self-supporting, filamentary electrically conductive member having first and second electrically insulated zones between which a portion of the member is exposed as an electrical contact.

The member preferably forms an endless loop.

11 Claims, 2 Drawing Sheets

ELECTRODE FOR ELECTRORETINOGRAPHY AND METHOD OF USE

This invention relates to an electrode for electroretinography (hereinafter ERG), to an electroretinography system, a method of measuring electrical potentials arising in the eye and to a method of applying an electrode to the human eye.

ERG involves electrical monitoring of electrical potentials arising from the eye following stimulation with light. This well established and widely used technique is an important diagnostic tool in ophthalmology, neurology and other fields of medicine. ERG is regarded as the only objective test for establishing the function of the retina and may, in certain diseases, reveal abnormalities before they are clinically evident or where they cannot be observed, for example due to opaque optic media.

Because the test does not necessarily require a patient's cooperation, it is also invaluable in the testing of visual function in infants and other groups of uncooperative patients.

From a clinical point of view, it is important and significant that ERG can be elicited either by bright flashes (flash ERG) or by contrasting light and dark elements alternating in phase (pattern ERG) since the two types of ERG are revealing of respective different generators of potential within the retina. Whilst the flash evoked ERG reveals diffuse retinal function, pattern evoked ERG generally reveals function of the central part of the retina by which colour and contrast discrimination are perceived. As a consequence of this, various types of electrodes for ERG recording are in use.

Reference may be made for example to "A Textbook of Clinical Neurophysiology" edited by Halliday, Butler and Paul, and published by John Wylie & Sons Ltd. in 1987. Page 579 of this work illustrates different types of corneal electrodes, including the contact lens electrode (Henkes type), the gold foil electrode and the DTL electrode.

The contact lens electrode has an outer annular cup holding a transparent plastics lens within which an electroconductive element is incorporated for detecting ocular potentials. Such electrodes are relatively stable and enable high amplitude signals to be obtained. However, they are suitable only for flash ERG recording since pattern discrimination requires the eye to have a free optic zone. In addition, they have the major drawback that they are relatively invasive and uncomfortable for patients to wear in spite of excessive local anaesthesia. They are therefore unsuitable for children and other uncooperative patients. Application has to be performed with extreme care and the eye has to be dressed with antibiotic ointment and a patch since minor ocular trauma is very likely to result.

The gold foil electrode consists of a thin "MYLAR" tape with a thin gold film provided on one side thereof. The thin tape is inserted in the lower fornix of the eye with the gold film in contact with the cornea. It is then taped into position on the lower eyelid. The electrode is claimed to be sufficiently non-invasive that it can be employed even without local anaesthetic drops. Although it is true that local anaesthesia is preferably avoided because patients may rub their eyes directly in the absence of a pain reflex, this is not a major problem and local anaesthesia is generally common in ophthalmic practice. Local anaesthesia is therefore often used also with the gold foil electrode in patients with excessively sensitive eyes because blinking and tears cause extremely noisy recordings. The gold foil electrode is especially recommended for pattern ERG technique although it may also be used with flash stimulation. It is capable of producing reasonably high amplitude responses but they are liable to be fairly inconsistent as a result of changing position and contact of the electrode caused by blinking and by excessive tears changing the contact conditions. Direct contact with the cornea is necessary and as a consequence minor corneal abrasions are likely to occur and have been reported. Furthermore, the electrode is very fragile, easily broken or bent and is fairly expensive. Moreover, each individual electrode cannot be used for an extended period of time. Cleansing and sterilizing is also difficult and the electrode is unsuitable for use with young children.

The DTL fine wire electrode comprises a fine wire which is placed under the lower eyelid. Although this may be somewhat less invasive than the gold foil electrode, it otherwise suffers from similar disadvantages. Another known electrode is the "DTL fibre electrode" using DTL fibre which is made up of filaments of spun nylon impregnated with silver. The filaments float on a tear film and make contact with an adjacent metal conductor. Normally, the impregnated nylon fibres are placed across the eye from one side to the other so that they touch the cornea at the centre. Although the electrode is non-invasive, it is extremely difficult to apply since it very easily loses contact or changes position. Extreme patient cooperation is therefore essential. It is therefore clearly unsuitable for young children.

Another known electrode is the silver disc electrode which was originally devised for electroencephalography recording. This consists of a chlorided silver disc which is usually glued onto the scalp. For ERG recording, it is simply taped onto the lower eyelid. The main drawback of this technique is the relatively low amplitude of potentials measured and thus the limited resolution power of the method itself. Furthermore, muscular action of the lower lid greatly interferes with the ocular signal. Additionally, before application of the electrode, the skin has to be cleansed with alcohol or acetone to reduce the skin resistance and this may cause irritation and tears, especially in children for whom this electrode is otherwise the most suitable option.

From the above discussion, it will be apparent that all known electrodes for ERG recording have serious drawbacks either in stability, ease of use, of magnitude and/or consistency of results. The contact lens electrode is the most stable and yields the largest response. However it is the most invasive and very unsuitable for use with children. It is also unsuitable for pattern ERG recording. As a result, it has been abandoned by most laboratories in this field. The gold foil electrode is fragile and unstable, frequently changes position during recording and requires highly cooperative subjects. It is therefore unsuitable for children. The same is basically true for the DTL fibre electrode and the DTL fine wire electrode. The disc electrode yields low responses coupled with a high level of muscular noise and although the best of all for children requires irritating cleansing of the skin with alcohol or acetone.

There is therefore a need for a versatile, non-invasive and effective electrode for ERG recording of large amplitude. This is especially important for pattern ERG signals which are generally small and variable, so that improved resolution of the method would widen diagnostic possibilities in neuroophthalmology.

According to a first aspect of the invention there is provided an electrode for electroretinography comprising a plastically deformable, self-supporting, filamentary, electrically conductive member having first and second electrically insulated zones between which a portion of the member is exposed as an electrical contact.

The member would normally be made of a noble metal such as gold, silver or platinum.

Preferably, the member forms a loop and has a signal extraction region spaced from the electrical contact.

The electrically conductive member is preferably formed from a plurality of strands of conductive material. Preferably the strands are woven together.

The electrical insulation is preferably a layer of "TEFLON".

The electrical contact is preferably an exposed window in a continuous portion of insulation extending into the first and second electrically insulated zones.

According to a second aspect of the invention, there is provided an electrode for electroretinography comprising: an endless plastically deformable, self-supporting, filamentary, electrically conductive member.

According to another aspect of the invention there is provided an electroretinography system for electrical monitoring of potentials arising after stimulation of an eye with light, comprising: an electrode according to the first or second aspect of the invention; signal detection apparatus; and an electrical conductor for coupling the electrode to the detection apparatus.

According to a further aspect of the invention there is provided a method of measuring electrical potential in the eye in which an electrode according to the first or second aspect of the invention is shaped to the contour of the eye, and inserted into the lower fornix of the eye.

A further aspect of the invention provides a method of applying an electrode according to the first or second aspect of the invention to an eye in which the electrode is bent to correspond to the curvature of the eye and form a hook which is hung over the lower eyelid with the electrical contact in the lower fornix of the eye.

For a better understanding of the invention and to show how the same may be carried into effect, reference will now be made by way of example to the accompanying drawings in which.

Figures 1, 2:
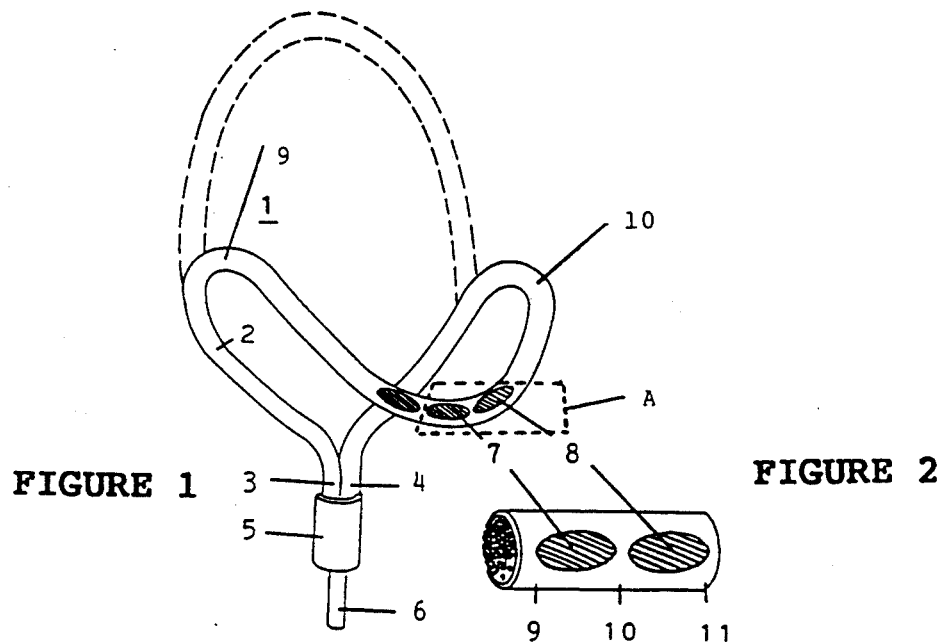
FIG. 1 shows a perspective view of an electrode for electroretinography according to one embodiment of the invention.
FIG. 2 shows an enlarged of the portion A of FIG. 1.

Referring first of all to FIG. 1, an electrode 1 for electroretinography is formed from a length of stranded silver wire 2, the ends 3 and 4 of which are soldered together and insulated by a plastics sleeve 5. A gold plated connector pin 6 is also soldered to the ends 3 and 4 within the sleeve 5. The whole length 2 of silver wire is insulated with polytetrafluoroethylene ("TEFLON") except in the central region where several rectangular windows, preferably three, are formed as illustrated more clearly in FIG. 2, which is an enlarged view of region A of FIG. 1 containing two windows 7 and 8. Of course, the insulation is removed from the silver wire within the insulating sleeve 5.

Since the wire loop 2 is formed of stranded silver wire, as appears more clearly from FIG. 2, it is plastically deformable and self-supporting in any position to which it is deformed. FIG. 1 illustrates the electrode in two different positions. The position illustrated in broken lines represents a flat loop of wire in a single plane. This is the configuration in which the electrode would normally be supplied to a user. The position illustrated in full lines is a configuration typical of that into which the electrode would be bent before use in electroretinography. This configuration will be discussed in more detail with reference to FIGS. 3 and 4. From the above discussion, it will be apparent that the electrode comprises an endless plastically deformable, self-supporting, filamentary electrically conductive member (the stranded silver core of the loop 2) which has first and second electrically insulated zones 9 and 10 between which portions of the member are exposed through windows 7 and 8 for use as electrical contact areas. The windows are provided over a length of about 1 cm on the side where the electrode touches the eyeball when in use.

Referring to FIG. 2, the "TEFLON" insulation extends as a bridging member 11 to separate the two windows 7 and 8. This is to prevent the wire being displaced from the sleeve during bending of the electrode.

The parts of the silver wire member exposed through the windows 7 and 8 are passivated by being chlorided. In the preferred embodiment the wire of the loop will be 4 cm in length and have a diameter of 0.20–0.30 mm. The gold plated pin 6 will preferably have a diameter of 0.4 mm.

Figures 3, 4:
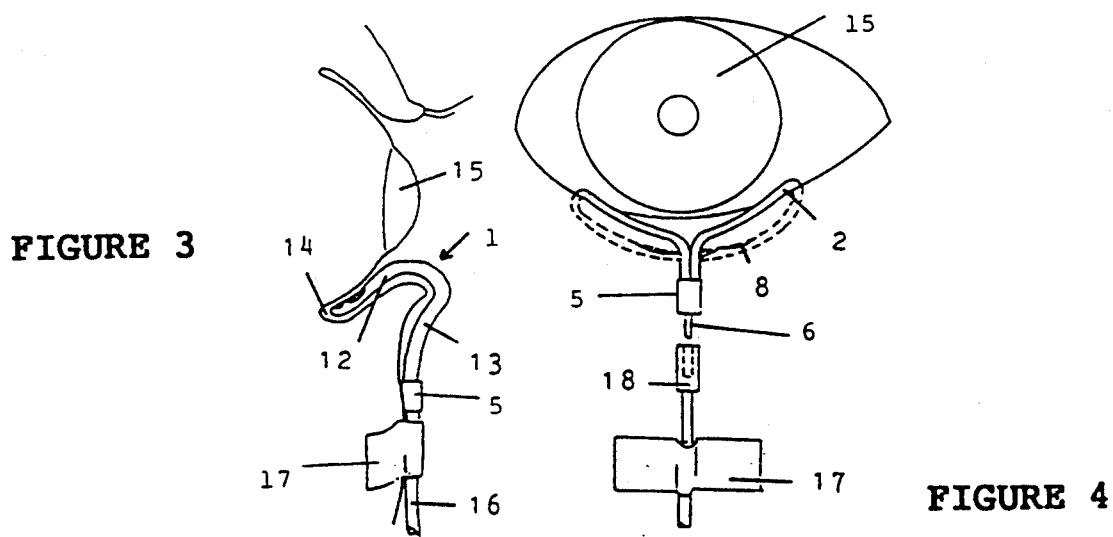
FIG. 3 shows a diagramatic lateral view of the electrode of FIG. 1 applied in the fornix of a human eye.
FIG. 4 shows a front view of the electrode in position on a human eye as in FIG. 3.

Referring now to FIG. 3, it will be seen that when in use the electrode is bent to a configuration which appears 'U' shaped in side view. The two limbs 12 and 13 of the 'U' shape together form a hooking member to enable the limb 12, carrying the windows 7 and 8 to be inserted into the lower fornix 14 of a human eye, having a cornea 15. It will be observed that no part of the electrode 1 is in contact with the cornea 15 when correctly inserted. The pin 6 extending from the sleeve 5 fits in a socket on an insulated copper connecting wire 16. The wire 16 is secured to the skin surface beneath the eye by means of tape 17.

Referring to FIG. 4, it will be seen more clearly how the loop shape of the electrode is able to avoid contact with the cornea 15. Furthermore, the loop configuration hooked into the fornix provides a stable secure mounting for the electrode, especially when the tape 17 has been applied. The socket for the pin 6 is shown at 18 in FIG. 4.

It will be apparent that the electrode is extremely easy to insert. It can be bent according to the particular anatomical configuration of the patient's eyelid, and thus be adapted to the normal variation, to children, or to any pathologically changed anatomy. It is very stable, and does not change its position while the patient is blinking. The insulation provided at either side of the windows 7 and 8 prevents potential loss due to contact with surrounding skin and excessive pick-up of muscular noise, thus ensuring that the signal obtained is of relatively large amplitude and is very consistent. Amplitude of the signal recorded following pattern stimulation is between 5 and 6 microvolts, which is about double the value produced by skin electrodes and in about the same range as the signal obtained by the gold foil electrodes or DTL fibre electrode. On the other hand, stability and consistency of response is much better than the gold foil or DTL fibre electrode.

The electrode is comfortable to wear and does not touch the cornea so that abrasions of the latter are very unlikely. It may be used without anaesthetic drops, although they would normally be employed in order to obtain the best possible response. Where the drops are applied, the electrode is practically undetectable by the patient. It can thus be easily applied for use with children without need for any previous rubbing of the skin and with very low risk of eye trauma.

Furthermore, the electrode can be worn for prolonged periods without any eye irritation and will give stable results over an entire recording session. It is therefore excellent also for research purposes.

Since the electrode does not interfere with the optics of the eye, it can be used either for flash or pattern ERG recording. It is much more durable than the gold foil or DTL electrodes and one can be used for a long time.

For repeated use, sterilization is easily performed by immersing the electrode in a sterilizing solution or it may even be autoclaved. For this purpose, the complete electrode is disconnected from the socket on the connecting wire.

Figure 5:
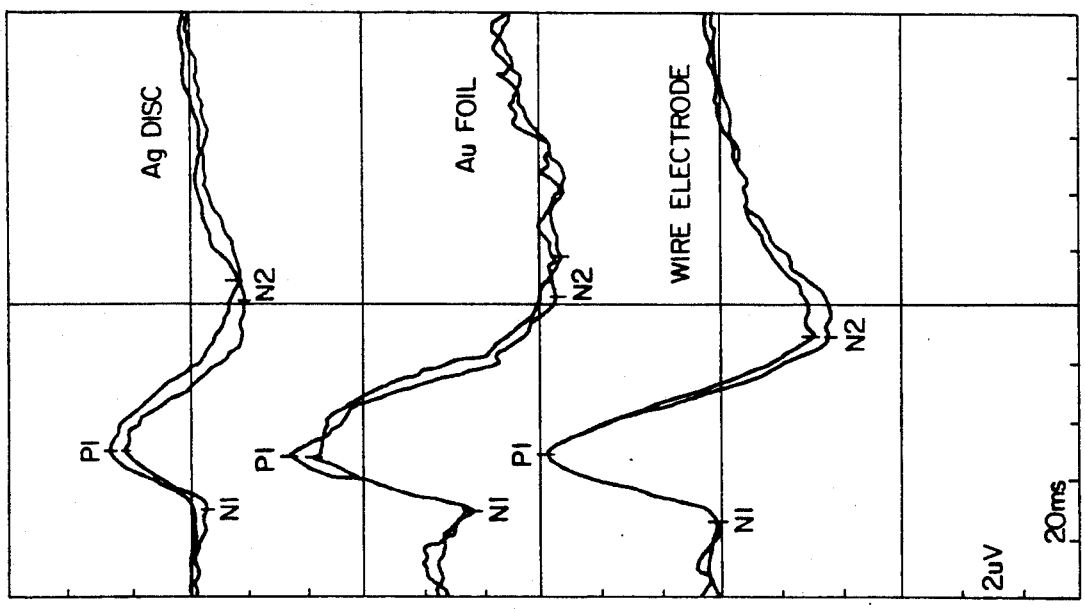
FIG. 5 shows voltage potentials measured using two types of known electrodes and an electrode according to the invention.

FIG. 5 shows pattern ERG signal output results obtained by means of the known silver disc electrode and by means of the wire electrode according to the embodiment illustrated in FIGS. 1 to 4. It will be observed that the signal (repeated twice) from the wire electrode (3rd line) is clean and consistent and of higher amplitude than that obtained with the silver disc electrode (1st line) and approximately of the same range as that obtained with a gold foil electrode (2nd line). For the silver disc electrode, mean amplitude (N1 to P1) of 2.85 microvolts was obtained whereas the equivalent amplitude was 5.70 microvolts for the wire electrode and 5.63 microvolts for the gold foil electrode. The average amplitude P1 to N2 for the wire electrode was as much as 9.00 microvolts. Measuring from the beginning of the trace, on average peak P1 occurred at 50.6 ms for the disc electrode, 49.7 ms for the gold foil electrode and 49.8 ms for the wire electrode, whereas peak N2 for the wire electrode occurred relatively early at 90.75 ms and was faster, cleaner and better reproducible than with silver disc or gold foil electrode.

I claim:

1. An electrode for electroretinography comprising: a plastically deformable, self-supporting, filamentary electrically conductive member having first and second electrically insulated zones between which a portion of the member is exposed as an electrical contact, said electrically conductive member being formed as a loop.

2. An electrode according to claim 1 wherein the electrically conductive member is of a noble metal.

3. An electrode according to claim 1, wherein the member is formed from a plurality of electrically conductive strands.

4. An electrode according to claim 1, wherein the member includes a signal extraction region spaced from the electrical contact.

5. An electrode according to claim 1, wherein two portions of said member are exposed between said insulated zones.

6. An electrode according to claim 1 wherein said exposed portion is exposed through a window in an otherwise continuous sleeve of insulating material unitary with insulating material in said insulated zones.

7. An electrode according to claim 1, wherein said insulated zones are insulated with polytetrafluoroethylene.

8. An electrode according to claim 1, wherein the said electrical contact is passivated.

9. An ERG system for electrical monitoring potentials arising after stimulation of an eye with light comprising: an electrode having a plastically deformable, self-supporting, filamentary electrically conductive member, said electrically conductive member being formed as a loop; signal detection apparatus; and an electrical conductor for coupling the electrode to the detection apparatus.

10. A method of measuring electrical potential from the eye comprising the steps of shaping a plastically deformable, self-supporting, filamentary, electrically-conductive member to the contours of the eye, said electrically conductive member being formed as a loop, inserting the member into the lower fornix of the eye, coupling the member to signal detection apparatus, and thereafter measuring electrical potentials from the eye.

11. A method of applying an electrode to an eye comprising the steps of bending a plastically deformable, self-supporting, filamentary, electrically-conductive member formed as a loop, a portion of which member provides an electrical contact, to correspond to the curvature of the eye and to form a hook and thereafter hanging the hook over the lower eyelid with the electrical contact of the electrode in the lower fornix of the eye.

* * * * *